125-850
47172 OR RE 32,275

United States Patent [19]

Zartman

[11] E Patent Number: Re. 32,275

[45] Reissued Date of Patent: Nov. 4, 1986

[54] INTRAVAGINAL ANCHORING DEVICE

[75] Inventor: David L. Zartman, Worthington, Ohio

[73] Assignee: New Mexico State University Foundation, Las Cruces, N. Mex.

[21] Appl. No.: 714,622

[22] Filed: Mar. 21, 1985

Related U.S. Patent Documents

Reissue of:

[64] Patent No.: 4,377,157
Issued: Mar. 22, 1983
Appl. No.: 194,583
Filed: Oct. 6, 1980

[51] Int. Cl.[4] ..... A61B 19/00

[52] U.S. Cl. ..... 128/1 R; 128/1 R; 128/345; 128/736

[58] Field of Search ..... 128/1 R, 127-131, 128/341, 343, 345, 736

[56] References Cited

U.S. PATENT DOCUMENTS

| | | | |
|---|---|---|---|
| 3,583,389 | 6/1971 | Harvey | 128/736 |
| 3,811,423 | 5/1974 | Dickinson et al. | 128/1 R |
| 3,811,424 | 5/1974 | Dickinson et al. | 128/1 R |
| 3,844,273 | 10/1974 | Polson | 128/738 |
| 3,971,362 | 7/1976 | Pope et al. | 128/736 X |
| 4,028,687 | 6/1977 | Hamaguchi et al. | 340/870.16 |
| 4,091,807 | 5/1978 | Dickinson et al. | 128/130 |
| 4,246,896 | 1/1981 | Horne, Jr. et al. | 128/130 |
| 4,387,724 | 6/1983 | Zartman | 128/736 |

OTHER PUBLICATIONS

"An Automatic System for the Measurement and Recording of Basal Temperature in the Human Female", *Fertility and Sterility*, 15:44-51, (1964) by Singer, M. D. et al.

"Continuously Telemetered Vaginal Temperature in the Baboon", *The Baboon in Medical Research, II*, Ed. H. Vagtborg, Univ. of Texas, Austin, pp. 19-35, (1967), by A. G. Hendrikx, Ph.D., et al.

The Detection of Ovulation by Intravaginal Telemetry", *Fertility and Sterility*, vol. 27, No. 9, (1976), John H. Mattox et al.

Hendricks, A. G. et al., "Continuously Telemetered Vaginal Temp. in the Baboon", from the Baboon in Med. Research II Ed., Univ. Texas Press, Austin (1967), pp. 19-35.

*Primary Examiner*—Dalton L. Truluck
*Attorney, Agent, or Firm*—Lane & Aitken

EXEMPLARY CLAIM

This invention relates to an improved device for intravaginal implantation in mammalian females characterized by an axially-extending hub encircled at both ends by a plurality of radially-extending springable spine-like fingers defining multi-pointed stars, the two stars being so located relative to one another and to the hub linking them together that no portion of the hub is left accessible to the vaginal wall musculature to a degree which will allow contortions thereof to expel the device while, at the same time, leaving sufficient hub exposed between the stars to receive and hold a small object no longer than it is nested within the fingers in protected relation.

9 Claims, 3 Drawing Figures

INTRAVAGINAL ANCHORING DEVICE

Matter enclosed in heavy brackets [ ] appears in the original patent but forms no part of this reissue specification; matter printed in italics indicates the additions made by reissue.

The prior art patented intravaginal device has, as its intended purpose, the "non-hormone, non-drug growth stimulant" for large mammalian females such as heifers and gilts. Early studies seemed to suggest that implantation of the device in the forward portion of the animal's vagina touching her cervix was effective to improve the weight-gain of the animals thus equipped, the theory being that when the cervix and vaginal walls are thus stimulated so-called "bulling" is reduced and better feed conversion results. The animal, of course, continues to go through her natural heat cycle and supposedly requires no heat suppressant drugs to reduce her sexual activity.

Unfortunately, the early expectations have proven to be unfounded in more recent studies conducted by later investigators. For instance, Bellows et al reported "Treatment of cows with the vaginal device did not significantly affect weight gains" (R. A. Bellows, et al "Beef Production From Mature Cows On Range Forage". J. Anim. Sci. (1979) 49:654). Other investigators also found no improvement in feed lot performance or any reduction in estrus activity in those animals equipped with the patented device. Significantly, however, many of these same investigators experienced considerable difficulty in keeping the device properly implanted in the animal for the long term it was claimed to stay in place.

G. M. J. Horton, et al "Intravaginal Devices For Feedlot Heifers". J. Anim. Sci. (1979) 49:915 reported 11 of 27 heifers had lost the implanted device at the time they were slaughtered. Interestingly, these investigators failed to ascertain any reason for the loss of the treatment device and, in fact, stated: "The reason for the high expulsion rate is not clear." The foregoing article contains a lengthy bibliography on other studies using the patented device which, for the most part, failed to produce the superior growth pattern predicted while saying little about its retention rate. Goodman et al, on the other hand, found no less than 43.8% of the heifers had lost one or more of the devices during the experiment and 6 of the 48 were without it at the time they were slaughtered (J. P. Goodman, et al "Hei-Gro Intravaginal Device And Synovex-H Implants For Feedlot Heifers" Annual (22nd, 1979) Cattle Feeders Day, South Dakota Agricultural Experiment Station, South Dakota State University.)

While earlier studies showed better retention, only one group of investigators seemingly had any explanation for the animal's ability to expel the device and their conclusion placed the blame on simultaneous treatment with another type of implant which they reasoned resulted in a stimulated vaginal mucus secretion accompanied by lengthening of the vaginal muscle cells, both of which cooperated "to allow easier passage of the device from the vagina." J. L. Lesmeister, et al. "Effect Of An Intravaginal Device On Heifer Weight Gain" Western Section, American Society of Animal Science. (1978) 29:89-90.

Applicant's objective was quite different from that of the makers of the "Hei-Gro" device in that he was unconcerned with growth stimulation, but rather, the long term intravaginal implantation of a miniature radiotelemetry device capable of transmitting very accurate deep body temperature data to a remote receiving station, such forming the subject matter of applicant's copending U.S. patent application Ser. No. 149,250 filed May 12, 1980. In another sense, however, despite the fact that applicant's objective and that of the "Hei-Gro" inventor differed, their basic needs were much the same, namely, a non-toxic device capable of non-surgical intravaginal implantation for long periods of time that would not impair the animal's physiological activity or prevent insemination while, at the same time, remaining safe to use. In addition, of course, applicant's implantable device had to possess the additional capability of being able to support and anchor the telemetry unit.

Of the commercially available devices designed for intravaginal implantation, two clearly failed to meet the above criteria. The first of these was the progesterone-soaked sponge or pessary insert for estrus and ovulation control. While answering the requirements of non-surgical implantation and those of being relatively safe and non-toxic, they failed the other two, namely, a device which does not interfere with insemination, treatment or the flow of natural secretions; and, the all-important long retention time. J. Sreenan reported a retention rate some 25% lower in cows than heifers and a better retention rate for a pessary having a density of about 0.018 gm./cc, however, the maximum retention time was far too short (20 days) to suit applicant's needs. J. Sreenan "Retention of intravaginal sponge pessaries by cattle." Vet. Rec. (1974) 94:45-47.

Another of the possible approaches to the solution of applicant's radio transmitter anchoring problem is the so-called "PRID" device marketed by Abbot Laboratories. Its function is one of hormonal stimulation, specifically progesterone, through the release of oestradiol. Mechanically, the "PRID" device is implanted non-surgically into the vagina and, of course, is non-toxic and relatively safe to use although a retrieval string is left hanging out of the entrance to the vagina which under some circumstances can be a source of irritation, physiological stress and even infection. It, like the pessary, constitutes a barrier within the vaginal tract which interferes with treatment thereof should such be necessary and, to an extent at least, the flow of natural secretions. Most important for present purposes, however, is its short retention time of twelve days which, once again, is far too short for applicant's long term deep body temperature monitoring needs. In fact, Roche found that none of the "PRID" devices was present in the vagina of ten heifers only 3 days later. Roche, J. F. "Rentention rate in cows and heifers of intravaginal silastic coils impregnated with progesterone.", J. Reprod. Fert. (1976) 46:253-255.

The only other viable solution to the problem known to applicant at this time is a vaginal ring wherein a stiff metal spring in the form of a closed loop was covered with a silicon polymer, specifically, Dow-Corning's "Silastic 382, medical grade." In one reported investigation, such rings were impregnated with Medroxyprogesterone Acetate and placed in a human female's vagina for contraceptive purposes. Daniel R. Mishell, Jr., M.D., et al "Contraceptive Effect of Varying Dosages of Progestogen in Silastic Vaginal Rings." Fertility and Sterility (1970) 21:99-103. At first glance, such a unit seemed to offer the solution to applicant's radio transmitter anchoring problem because, not only was it implantable non-surgically but, in addition, it could be left in place for prolonged periods without interfering with normal bodily functions including both natural and artificial insemination. Other investigations (A. G. Hendrickx, Ph.D., et al "Continuously Telemetered Vaginal Temperature in the Baboon ', The Baboon in Medical Research, II. Ed. H. Vagtborg. Univ. of Texas Press (1967 pp 19-35) in advance of applicant including Mishell et al (supra) rather clearly established the fact that such rings would remain in place for the time periods required by applicant to obtain the necessary background temperature data against which an estrus-caused deviation could be detected; however, these units failed to answer applicant's needs for other reasons. In the human female study, there was some irritation evident but a more serious complication developed, namely, erosion and ulceration of the vaginal mucosa. In the baboon study, while no serious side effects were evident, the unit failed for other reasons. To begin with, the telemetry unit failed after only a maximum of 24 days of in situ use. Conceivably, of course, this problem could be solved and, as a matter of fact, applicant's radio transmitter has survived long in situ periods while continuing to perform quite satisfactorily. The most disturbing finding of the Hendrickx et al (supra) baboon study was the fact that each animal had to be individually fitted with the device. This, of course, renders such a technique totally suitable for range cattle and other ordinary livestock since the time and expense involved in carrying out a program involving hundreds of animals would be prohibitively expensive.

To his dismay, applicant was left without a single non-surgically implantable device that could be employed to anchor a small radio transmitter in the vaginal canal of a mammalian female that would remain in place for prolonged periods of time and not interfere with normal functions involving the implantation site until, quite unexpectedly, it occurred to him that it was not, as others found, the simultaneous administration of medicaments that caused both relaxation of the vaginal walls and increased secretions therein that rendered the latter slippery and unable to retain the "Hei-Gro" device, but rather, the presence of the long projecting stem and cone-like end on the commercially available unit that apparently enabled the animal's uterine contractions to eventually expel same. Accordingly, after confirming what others had already found that the commercially available "Hei-Gro" device was easily expelled by the animal's implanted therewith, applicant removed from the standard "Hei-Gro" unit the projecting stem and cone-like appendages and left both extremities of the hub encircled by a plurality of radially-projecting flexible fingers. His efforts in this regard proved quite rewarding since even when fitted with a miniature battery-powered telemetry device buried within the confines of the so-called stars, the animal was unable to dislodge same except under rare circumstances. Moreover, such an implant produced no untoward side effects, the animal remained calm and her normal bodily functions involving the uterine canal including both natural and artificial insemination remained unimpaired.

It is, therefore, the principal object of the present invention to provide a novel, improved, much simplified and more effective intravaginal anchor of the general type sold under the trademark "Hei-Gro".

A second objective is the provision of a device of the type aforementioned which is devoid of externally accessible appurtenances such as strings and the like that can prove to be a source of irritation and serious infection.

Another object is the provision of a modified "Hei-Gro" type unit for intravaginal implantation that has vastly superior retention capabilities when compared with any known previous form thereof.

An additional objective is to provide an intravaginally-implantable unit patterned after the commercially available "Hei-Gro" device which has as its purpose the long term anchoring of other miniaturized equipment rather than the growth stimulation potential for which it was originally designed.

Further objects of the instant invention are to provide a non-surgically implantable intravaginal anchor which is safe, not toxic, does not interfere with natural physiological functions involving the vaginal canal, produces no untoward side effects, is inexpensive, requires no individual fitting, and a device of the class described that can be both installed and removed under range conditions by one possessing no special skills.

Other objects will be in part apparent and in part pointed out specifically hereinafter in connection with the description of the drawings that follows, and in which.

Figure 1:
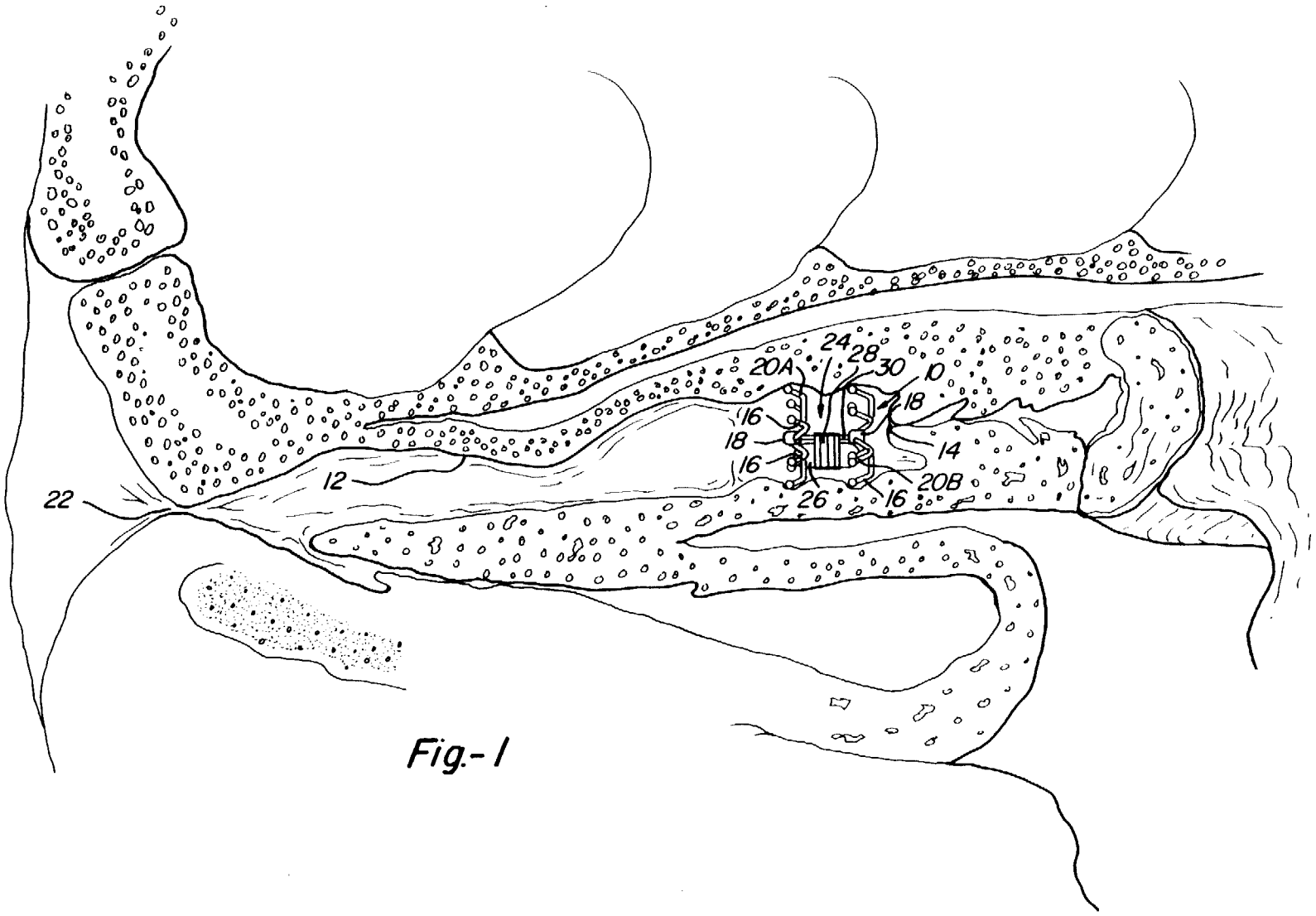
FIG. 1 is a diagram showing placement of the anchor along with its associated telemetry device within the vagina of a bovine female at the mouth of her cervix.

Referring next to the drawings for a detailed description of the present invention and, initially, to FIG. 1 for this purpose, it will be seen that the anchoring device which has been broadly designated by reference numeral 10, is implantable using well-known techniques within the vagina 12 of a mammalian female at the mouth of the cervix 14, the particular anatomy illustrated being that of a cow or heifer. The method of implantation is simply one of collapsing the radially-extending spider-like legs 16 emanating from the hub 18 of each star 20 preparatory to placing same in a speculum tube (not shown). Upon insertion of such a tube through the vulva opening 22 and ejecting the anchor from such tube by means of a pushrod or the like (not shown) the placement of the unit is complete. Suitable precautions are, of course, taken to insure that no injury of the delicate tissue in the vaginal area takes place and that the entire procedure is carried out under antiseptic conditions.

Figure 3:
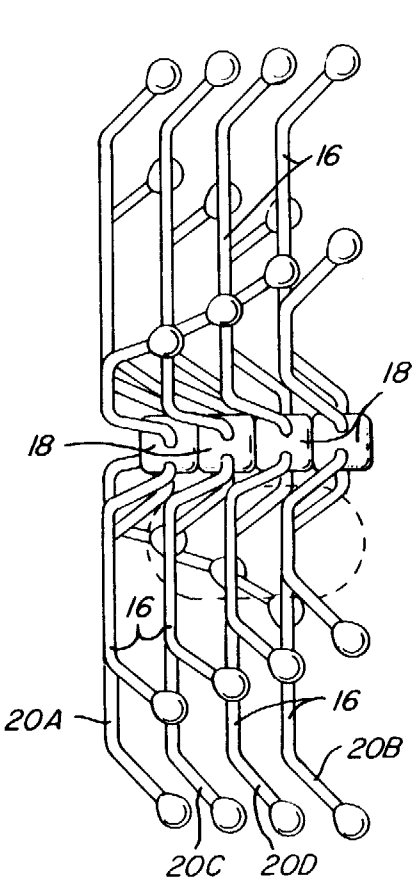
Figure 2:
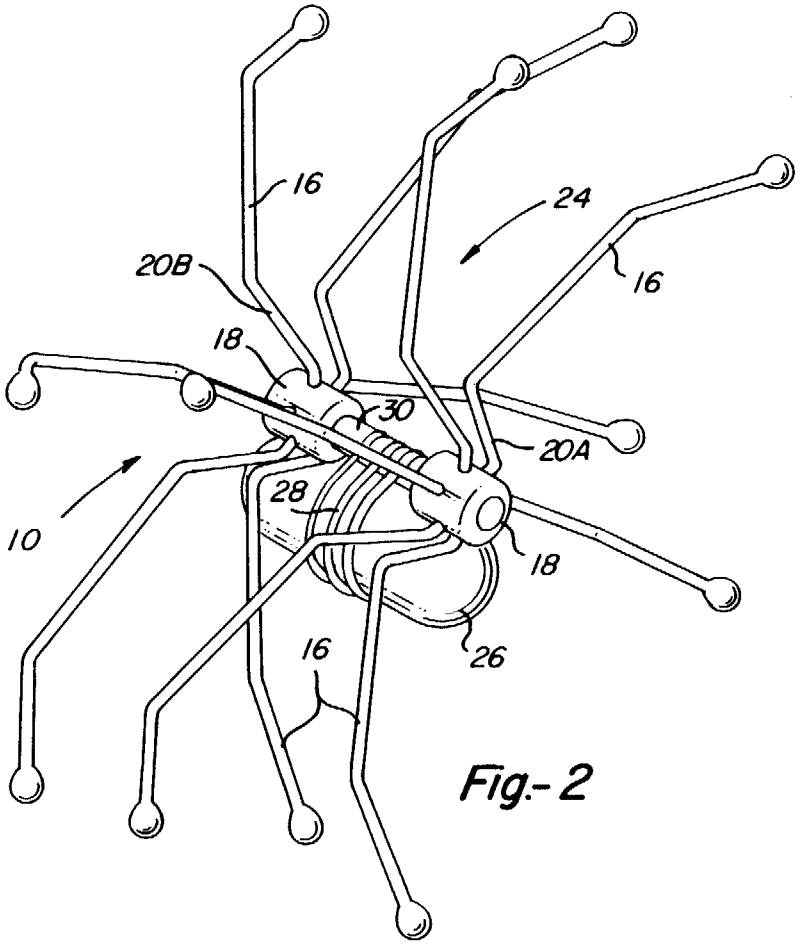
FIG. 2 is a perspective view to a greatly enlarged scale showing the implantable subassembly that includes both the modified "Hei-Gro" anchor and the battery-powered deep body temperature transmitter it is designed to carry; and, FIG. 3 is a side elevation of the anchor alone, the telemetry device and its spatial relation to the latter having been indicated by phantom lines.

As soon as the anchor 10 leaves the trochar tube, its arms 16 spring open and assume the unfolded or expanded operative condition shown in all three figures of the drawings. If, as shown in FIGS. 1 and 2 in full lines and in phantom lines in FIG. 3, the anchor 10 is but a part of an assembly 24 that includes a battery-powered radio transmitter 26 and some means 28 for fastening the latter to the hubs 18 intermediate the stars 20 on opposite ends thereof, then the speculum tube must be sized to accommodate the entire assembly while, at the same time, remaining small enough to pass easily through the vulva opening. Applicant has been successful in locating a battery-powered telemetry device capable of transmitting accurate temperature measurements to a remote receiving station located outside the animal's body that is only about the size of the end of an adult's thumb. Using such a radio transmitter, the standard size "Hei-Gro" speculum tube accepted the assembly quite easily.

FIGS. 1 and 2 to wh ch detailed reference will next be made both show the 2-star version of the anchor in which identical stars 20 are spaced apart axially about ¾ inches with an axially-extending stem member 30 being used to interconnect the hollow hubs 18 of the two stars. As illustrated in FIG. 2, the fastening means 28 comprises a short length of sterile cord or suture material tying the transmitter to the exposed medial portion of the stem. The 2-star version of the anchor 10 has proven quite satisfactory for use in heifers and small cows as the data in Table I which follows, indicates:

TABLE I

| Animal | Device | Expelled[1] | Retained |
|---|---|---|---|
| CATTLE | | | |
| Heifer 1464 | Unmodified Hei-Gro 2-star | X | |
| Heifer 1464 | Unmodified Hei-Gro 2-star | X | |
| Heifer 1494 | Unmodified Hei-Gro 2-star | X | |
| Heifer 1464 | Unmodified Hei-Gro 2-star | X | |
| Heifer 1474 | Modified coneless 4-star | | X |
| Heifer 1494 | Modified coneless 4-star | | X |
| Cow 690[2] | Modified coneless 2-star | X | |
| Heifer 1464 | Modified coneless 2-star | | X |
| Cow 690[2] | Modified coneless 4-star | X | |
| Cow 690[2] | Modified coneless 6-star | | X |
| Heifer 1464 | Modified coneless 4-star | | X |
| Cow F-35 | Modified coneless 2-star | | X |
| Cow 971 | Modified coneless 2-star | | X |
| Cow 944 | Modified coneless 2-star | | X |
| Cow 1302 | Modified coneless 4-star | | X |
| Cow 1426 | Modified coneless 4-star | | X |
| Cow 1312 | Modified coneless 4-star | | X |
| Cow 1478 | Modified coneless 4-star | | X |
| HORSES | | | |
| Mare Celcida | Unmodified Hei-Gro 2-star | X | |
| Mare Angelique | Modified coneless 4-star | | X |
| Mare Celcida | Modified coneless 2-star | | X |
| Mare Celcida | Modified coneless 4-star | | X |
| Mare #1 | Modified coneless 4-star | | X |
| Mare #2 | Modified coneless 4-star | | X |
| Mare #3 | Modified coneless 4-star | | X |
| Mare #4 | Modified coneless 4-star | | X |
| Mare #5 | Modified coneless 4-star | | X |
| SWINE | | | |
| Sow #1 | Modified coneless 2-star | X | |
| Sow #2 | Modified coneless 2-star with shortened arms | | X |

[1]The device was visible at the vulvar opening or completely out
[2]An extremely large cow of old age As the above data reveals, not one of the standard "Hei-Gro" devices remained in place and applicant suspects that the animal's vaginal contortions were responsible for its ultimate expulsion although this is difficult to verify. Of the 7 mares and 11 cows implanted with the anchor 10 modified in accordance with the teaching found herein so as to remove therefrom the entire stem and cone portion leaving only the stars 20 and whatever connecting portion 30 of the stem that is left therebetween, only one animal was able to expel it and she happened to be an old cow with an extremely large body (well in excess of 1500 pounds) and an oversize reproductive tract. She was even able to expel the 4-star version of the anchor shown in FIG. 3 where two additional stars 20C and 20D are interposed between stars 20A and 20B found in both the 2-star and 4-star versions. When fitted, however, with a 6-star version (not shown) containing yet another two stars 20, even she was unable to expel it. For by far the majority of heifers and cows the 4-star version is entirely adequate and should result in essentially 100% retention over extended periods of time, say 50 days and longer. In extreme cases like Cow 690, the preferred unit would be the 6-star version and, for lack of a better criteria, a body weight in excess of 1500 pounds would almost surely cover those animals requiring the largest of the three anchors. A 2-star unit has proven quite adequate as an anchoring device for holding small objects in the vagina of cows, heifers and mares of reproductive age although, to be on the safe side, the 4-star version is preferable for use in the more mature females.

The length of the arms 16 in the standard "Hei-Gro" unit measured between opposite ends thereof seems to average somewhere slightly in excess of 6 cm. Applicant has found that for smaller mammalian females like, for example, sows and ewes, a further modified unit having stars with arm lengths of only about 3.5 cm. proved quite adequate. As a matter of fact, the full size 2-star modified unit apparently was too large to be inserted all the way to the entrance of the cervix since it remained clearly visible at the vulvar opening.

Accordingly, applicant has been successful in cleverly modifying the commercially available "Hei-Gro" growth promotion device so as to convert the latter to anchoring device capable of holding small objects in situ within the vagina of mammalian females of various species and sizes for prolonged periods of time while, at the same time leaving their normal reproductive functions unimpaired.

What is claimed is:

1. In a device for intravaginal implantation in mammalian females which includes an axially-extending hub having an anterior end and a posterior end and being encircled by a ring having a plurality of radially-extending springable spine-like fingers thereon, said ring cooperating with said hub to define a multi-pointed star, an improvement consisting of an anterior star having a ring located substantially flush with said hub anterior end and a posterior star having a ring located substantially flush with said hub posterior end, said posterior star being in axially-spaced relation to said anterior star to leave a section of said hub exposed between said stars, the fingers of both stars being shaped to spring forwardly into folded relation in response to a radially-directed pressure exerted upon the ends thereof remote from the hub, and the length of the fingers on the posterior star in relation to said exposed hub section being such that when the posterior star fingers are sprung forwardly into folded relation along the exposed hub section said fingers overlie the exposed length of said hub and are effective to prevent engagement between the exposed hub section and the vaginal musculature.

2. The improved intravaginal device of claim 1 wherein the hub and fingers of the stars at opposite extremities thereof cooperate to define means for anchoring a small object no longer than the hub in nested protective relation among the fingers.

3. The improved intravaginal device of claim 1 wherein additional rings of radially-extending spring-like fingers emanate from the hub defining at least one additional star located intermediate the stars on the extremities of the hub.

4. The improved intravaginal device of claim 1 wherein the overall axial length is substantially less than the radius of the circle defined by the stars.

*5. The device of claim 1, wherein said fingers define openings such that fluids can freely pass therethrough, and wherein said device further comprises a biasing means to urge said fingers forward, a means for retaining a telemetry device for transmitting data from said vagina to a remote receiving station, and said telemetry device retained by said retaining means.*

*6. The device of claim 5 wherein said telemetry device is retained in between said expandable members.*

*7. The device of claim 5 wherein said telemetry device comprises a temperature sensing means, whereby at least intravaginal temperature data are transmitted to said remote receiving station.*

*8. A system of monitoring intravaginal data of a plurality of livestock animals comprising said remote receiving station and a plurality of the devices of claim 5 disposed on a range intravaginally within said animals.*

*9. The system of claim 8 wherein said telemetry device comprises a temperature sensing means, whereby at least intravaginal temperature data are transmitted to said remote receiving station.*

* * * * *